United States Patent
Cambou et al.

(10) Patent No.: US 11,576,405 B2
(45) Date of Patent: Feb. 14, 2023

(54) PALATABILITY ENHANCERS COMPRISING AMINO REACTANTS AND CARBONYL COMPOUNDS FOR USE IN CAT FOOD

(71) Applicant: SPECIALITES PET FOOD, Elven (FR)

(72) Inventors: Stéphanie Cambou, Vannes (FR); Cécile Niceron, Elven (FR)

(73) Assignee: SPECIALITES PET FOOD, Elven (FR)

(*) Notice: Subject to any disclaimer, the term of this patent is extended or adjusted under 35 U.S.C. 154(b) by 0 days.

(21) Appl. No.: 16/782,868

(22) Filed: Feb. 5, 2020

(65) Prior Publication Data

US 2020/0245645 A1 Aug. 6, 2020

Related U.S. Application Data

(62) Division of application No. 15/311,133, filed as application No. PCT/IB2014/001071 on May 15, 2014, now abandoned.

(51) Int. Cl.
| | | |
|---|---|---|
| A23K 50/40 | (2016.01) | |
| A23L 27/21 | (2016.01) | |
| A23K 20/147 | (2016.01) | |
| A23K 20/142 | (2016.01) | |
| A23K 20/163 | (2016.01) | |

(52) U.S. Cl.
CPC ............ *A23K 50/40* (2016.05); *A23K 20/142* (2016.05); *A23K 20/147* (2016.05); *A23K 20/163* (2016.05); *A23L 27/215* (2016.08)

(58) Field of Classification Search
CPC .. A23K 20/142; A23K 20/147; A23K 20/163; A23K 50/40; A23L 27/215
USPC ......................................................... 426/535
See application file for complete search history.

(56) References Cited

U.S. PATENT DOCUMENTS

| | | | |
|---|---|---|---|
| 3,697,287 A | 10/1972 | Winitz | |
| 4,466,986 A * | 8/1984 | Guggenbuehler | .... A23L 27/215 426/533 |
| 6,562,391 B1 * | 5/2003 | Vauthey | ................. A23L 27/215 426/533 |
| 6,660,319 B1 | 12/2003 | Shi et al. | |
| 2009/0098267 A1 | 4/2009 | Pettelot et al. | |
| 2009/0297662 A1 | 12/2009 | Kawaguchi et al. | |
| 2011/0189367 A1 | 8/2011 | Sagalowicz et al. | |
| 2013/0260000 A1 | 10/2013 | Lian Hwee Peng et al. | |
| 2014/0134306 A1 | 5/2014 | Sakaji et al. | |

FOREIGN PATENT DOCUMENTS

| | | |
|---|---|---|
| EP | 0 878 135 A1 | 11/1998 |
| FR | 2 012 745 | 3/1970 |
| GB | 1232719 A | 5/1971 |
| JP | 2005-198505 A | 7/2005 |
| JP | 2009-534020 A | 9/2009 |
| JP | 2011-526781 A | 10/2011 |
| JP | 2013-17470 A | 1/2013 |
| JP | 2013-208134 A | 10/2013 |
| WO | WO 2007/053713 A2 | 5/2007 |
| WO | WO 2007/118876 A1 | 10/2007 |
| WO | WO 2008/069173 A1 | 6/2008 |
| WO | WO 2013007639 A1 | 1/2013 |

OTHER PUBLICATIONS

Australian Office Action, dated May 3, 2018, for Australian Application No. 2014394376.
English translation of Japanese Office Action, dated May 8, 2018, for Japanese Application No. 2016-567738.
International Preliminary Report on patentability for PCT/IB2014/001071 (PCT/IPEA/409) dated Aug. 26, 2016.
International Search Report for PCT/IB2014/001071 (PCT/ISA/210) dated Jan. 29, 2015.

* cited by examiner

*Primary Examiner* — Walter A Moore
(74) *Attorney, Agent, or Firm* — Birch, Stewart, Kolasch & Birch, LLP

(57) ABSTRACT

The present invention concerns a non-fatty palatability enhancer for use in cat food comprising an amino reactant having a ratio AAS/AAT of sulfur-containing free amino acids (AAS) to total free amino acids (AAT) from 1 to 12.8% by weight, and a carbonyl composition comprising more than 20% up to 100% by weight of monosaccharides and/or disaccharides and/or oligosaccharides.

4 Claims, No Drawings

PALATABILITY ENHANCERS COMPRISING AMINO REACTANTS AND CARBONYL COMPOUNDS FOR USE IN CAT FOOD

CROSS REFERENCE TO RELATED APPLICATIONS

This application is a Divisional of copending application Ser. No. 15/311,133, filed on Nov. 14, 2016, which is a national phase of PCT International Application No. PCT/IB2014/001071 filed on May 15, 2014, all of which are hereby expressly incorporated by reference into the present application.

The present invention generally relates to the field of pet food and is more specifically focused on cat food.

More precisely, the present invention concerns a non-fatty palatability enhancer for use in cat food comprising an amino reactant having a ratio AAS/AAT of sulfur-containing free amino acids (AAS) to total free amino acids (AAT) from 1 to 12.8% by weight, and a carbonyl composition comprising more than 20% and up to 100% by weight of monosaccharides and/or disaccharides and/or oligosaccharides.

BACKGROUND OF THE INVENTION

Pets are well taken care of by their owners which provide them a proper selection of foods. Those foods include not only pets' usual nutritionally-balanced diet, but also supplements, treats, and toys. Pets, like humans, are attracted to and eat more regularly and easily foods which they find palatable. Therefore, palatability enhancers (PEs) are extremely important for animal consumption. Animal foods such as pet foods typically contain flavour compositions to increase the palatability thereof, and to make them appealing to pets. A large number of PEs have been described so far.

However, food palatability differs not only from one type of food to another, but also from one animal species to another. For example, a palatability enhancer effective in dry pet foods is usually not effective when used in semi-dry or wet pet foods. Moreover, a palatability enhancer effective with dogs is often not effective with cats. Indeed, cats are particularly known as being finicky because of their high susceptibility to food palatability.

There is therefore a continuing need for new PEs, which provide a robust flavour and which are easily and effectively usable for cats, in types of foods as different as dry, semi-dry and wet foods.

The present invention here provides new PEs that have been selected for their ability to enhance palatability of cat food.

SUMMARY OF THE INVENTION

An object of the present invention concerns a non-fatty PE for use in cat food comprising an amino reactant characterized by a ratio AAS/AAT of sulfur-containing free amino acids (AAS) to total free amino acids (AAT) from 1 to 12.8% by weight, and a carbonyl composition comprising more than 20% and up to 100% by weight of monosaccharides and/or disaccharides and/or oligosaccharides.

Another object of the present invention is related to a palatability-enhancing composition (PEC) for use in cat food comprising a PE of the invention.

Further objects of the present invention relate to methods for preparing PEs and PECs.

It is another object of the present invention to provide a method for producing a cat food having enhanced palatability.

A further object of the present invention concerns a kit for enhancing palatability of a cat food.

DETAILED DESCRIPTION OF THE INVENTION

Definitions

Percentages are expressed herein by weight of a product reference (in particular, a PE or a PEC). In some instances that will be apparent to the person skilled in the art, percentages may be expressed on a dry matter basis. The person skilled in the art will appreciate that the term "dry matter basis" means that an ingredient's concentration or percentage in a composition is measured after the free water has been removed, or determined on the basis of the weight of the composition once the weight of any free moisture in the composition has been subtracted.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 (from 0.1 to 1) represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

The terms "more than 20% and up to 100%" or "more than 20% up to 100%" mean herein a range starting from a value strictly superior to 20% and ending at 100%, i.e., all intermediate values between 20 and 100% are encompassed whereas the lower terminal value 20% is not.

As used throughout, the singular form of a word includes the plural, and vice versa, unless the context clearly dictates otherwise. Thus, the references "a", "an", and "the" are generally inclusive of the plurals of the respective terms. For example, reference to "a method" or "a food" includes a plurality of such "methods" or "foods". Similarly, the words "comprise", "comprises", and "comprising" are to be interpreted inclusively. Likewise the terms "include", "including" and "or" should all be construed to be inclusive. All these terms however have to be considered as encompassing exclusive embodiments that may also be referred to using words such as "consist of".

The methods and products and other embodiments exemplified here are not limited to the particular methodologies, protocols, and reagents that are described herein because, as the skilled artisan will appreciate, they may vary.

Unless defined otherwise, all technical and scientific terms, terms of art, and acronyms used herein have the meanings commonly understood by the skilled artisan in the field(s) of the invention, or in the field(s) where the term is used. Although any products, methods, or other means or materials similar or equivalent to those described herein can be used in the practice of the present invention, the preferred products, methods, or other means or materials are described herein.

The term "about" as used herein when referring to a measurable value such as an amount, a temporal duration, and the like, is meant to encompass variations of ±10%, more preferably ±5%, even more preferably ±2% from the specified value, as such variations are appropriate to reproduce the disclosed methods and products.

As used herein, the term "palatability" refers to the overall willingness of a pet to eat a certain petfood. Whenever a pet shows a preference, for example, for one of two or more petfoods, the preferred petfood is more "palatable", and has "enhanced palatability". Such preference can arise from any of the pet's senses, but typically is related to, inter alia, taste, aroma, flavour, texture, smell and/or mouth feel.

Different methods exist to assess palatability. Examples of such methods involve exposure of pets to petfoods either simultaneously (for example, in side-by-side, free-choice comparisons, e.g., by measuring relative consumption of at least two different petfoods), or sequentially (e.g., using single bowl testing methodologies). Advantageously, at least two different methods may be used to consolidate the thus obtained results on palatability of a given petfood.

A pet food, more particularly a cat food, that is stated herein to have "enhanced palatability" is one for which a cat exhibits preference relative to a control composition. Advantageously, a cat food having enhanced palatability is appealing or pleasing not just to cats, but to cat owners as well.

From a functional point of view, the terms "palatability enhancers (PEs)", "palatants", "flavours", "palatability agents", "appetizing factors", "flavour compositions", "palatability-enhancing compositions (PECs)", "flavour enhancers", and any other similar terms equivalently mean any material that enhances the palatability of a food composition to a cat. Typically, a palatability enhancer for cat food is an edible composition that provides an aroma, taste, aftertaste, smell, mouth feel, texture, and/or organoleptic sensation that is appealing or pleasing to the cat.

For example, a palatability enhancer may contribute to initial food appeal by its smell and/or to continued consumption by its smell but also by its taste and/or its aftertaste, and/or its mouth feel, and/or its texture. "Initial appeal" is an aspect of palatability that induces an animal (here, a cat) to initially taste or try a food, and that can be measured by the criteria "first choice" or "first food consumed". "Continued consumption" is an aspect of palatability that induces an animal (here, a cat) to continue consuming a food that has been initially only tasted or tried.

From a structural point of view, the terms "palatability enhancers (PEs)", "palatants", "flavours", "palatability agents", "appetizing factors", "flavour compositions", "palatability-enhancing compositions (PECs)", "flavour enhancers", and any other similar terms may refer to a single material or a blend of materials, that may be natural, processed or unprocessed, synthetic, or part of natural and part of synthetic materials.

Despite their equivalent functional meaning, each of the terms "palatability enhancers (PEs)", "palatants", "flavours", "palatability agents", "appetizing factors", "flavour compositions", "palatability-enhancing compositions (PECs)", "flavour enhancers" can advantageously be used to identify a specific material or blend of material in order to facilitate a proper distinction between various materials or blends of materials that all have advantageous palatability-enhancing properties. In particular, in the present context and as described below, a PE can be contained in a PEC.

As used herein, a "non-fatty PE" is a PE which does not contain any added or exogenous fat. In other words, a "non-fatty PE" according to the present invention only comprises the endogenous fat, if any, that may be contained in the amino reactant and the carbonyl compound. Thus, the fat content of the "non-fatty PE" according to the invention is very low, or even insignificant, or even undetectable by standard methods (such as described in European Regulation EC n° 152/2009 Determination of crude oils and fats—Procedure B—available online), and it may be referred to as "traces of fat".

The present invention is dedicated to cats.

As used herein, the term "cat food" or "food" means a product or composition that is eaten by a cat and provides at least one nutrient to the cat. The term "food" includes any food, feed, snack, food supplement, treat, toy (chewable and/or consumable toys), edible meal substitute, or edible meal replacement. Drinks and beverages of any type are encompassed within the term "food."

There are three main categories or classes of pet foods, in particular of cat foods, depending on their moisture content, which is either low or medium or high:
- dry or low moisture-containing products (having less than about 14% moisture): they usually produce a crunching sound when chewed by pets, in particular by cats; they are generally highly nutritious, may be inexpensively packaged (e.g., in bags or boxes), and are highly convenient to store and use; they are relatively shelf-stable and resistant to microbial or fungal deterioration or contamination;
- canned or wet or high moisture-containing products (having more than about 50% moisture): typically high meat-containing products, they are usually costly to produce and package (mainly in cans); they are not shelf-stable when opened so that excess or unused wet food must be refrigerated to prevent microbial or fungal spoilage;
- semi-moist or semi-dry or soft dry or soft moist or intermediate or medium moisture-containing products (having from about 14 to about 50% moisture): they are usually packaged in appropriate bags or boxes; they contain stabilizing agents and can thus be stored in the same way as dry products.

Nutritionally-balanced pet foods, in particular cat foods, are widely known and used in the art.

A "nutritionally-complete", "nutritionally-balanced" or "complete and nutritionally-balanced food" is one that contains all known required nutrients for the intended recipient or consumer of the food, in appropriate amounts and proportions based, for example, on recommendations of recognized or competent authorities in the field of companion animal nutrition. Such foods are therefore capable of serving as a sole source of dietary intake to maintain life, without the addition of supplemental nutritional sources.

The term "kibble" used herein refers to particulate chunks or pieces formed by either a pelleting or extrusion process. Typically, kibbles are produced to give dry and semi-moist pet food. The pieces can vary in sizes and shapes, depending on the process or the equipment. For instance, kibbles can have spherical, cylindrical, oval, or similar shapes. They can have a largest dimension of less than about 2 cm for example.

The term "chunk-in-"X" products" mean herein all edible foodstuffs comprising chunks in a preparation (said preparation being "the X preparation"). Classical examples thereof are chunk-in-jelly products, chunk-in-gravy products, and the like. This category of "chunk-in-X" products encompasses also edible forms other than chunks that may be contained in the X preparation such as a jelly, a gravy, and the like. For instance, other forms than chunks may be sliced products, grated products, etc.

The term "loaf" used herein refers to edible foodstuffs obtained as moist products, and includes terrines, pâtés, mousses, and the like.

The term "food supplement" or "dietary supplement" or "supplement" means a product that is intended to be eaten in addition to the normal animal diet. Drinks and beverages are encompassed. Dietary supplements may be in any edible form, e.g., solid, liquid, gel, paste, tablets, capsules, powder, and the like. Preferably they are provided in convenient dosage forms. In some embodiments, they are provided in bulk consumer packages such as bulk powders. In other embodiments, supplements are provided in bulk quantities to be included in other food items such as snacks, treats, supplement bars, and the like. PEs and PECs can be used to improve palatability of dietary supplements in the same manner as they are used to improve palatability of nutritionally-balanced foods.

The term "treat" (or "biscuit") means any food item that is designed to be fed to a pet (here, a cat), preferably at non-meal time, by the owner to help, promote or sustain a bonding process between a pet (here, a cat) and its owner. Examples of treats for cats are stuffed pillows and chewable sticks. Treats may be nutritional or not. Treats often contain PEs or PECs in a manner comparable to nutritionally-balanced foods.

"Toys" include, for example chewable toys. Examples of toys for cats are chewable cat toys. Toys further include partially consumable toys (e.g., comprising plastic components) or fully consumable toys (e.g., rawhides).

As used herein, the term "amino acid" means a molecule containing both an amino group and a carboxyl group. In some embodiments, the amino acids are $\alpha$-, $\beta$-, $\gamma$- or $\delta$-amino acids, including their stereoisomers and racemates. As used herein, the term "L-amino acid" denotes an $\alpha$-amino acid having the L configuration around the $\alpha$-carbon, that is, a carboxylic acid of general formula $CH(COOH)(NH_2)$-(side chain), having the L-configuration. The term "D-amino acid" similarly denotes a carboxylic acid of general formula $CH(COOH)(NH_2)$-(side chain), having the D-configuration around the a-carbon. Side chains of L-amino acids can include naturally occurring and non-naturally occurring moieties. Non-naturally occurring (i.e., unnatural) amino acid side chains are moieties that are used in place of naturally occurring amino acid side chains in, for example, amino acid analogs.

By the term "amino reactant" or "amino acid source", it is meant a reactant having a free amino group that is available to react with a carbonyl compound in a Maillard reaction. Amino reactants include amino acids, hydrolysates and extracts of peptides (including dipeptides, tripeptides, and oligopeptides) and proteins, hydrolysed vegetable protein (HVPs), peptones, yeast extracts, yeast hydrolysates, yeast autolysates, cream yeasts, soy sauces, and mixtures thereof.

By the term "free amino acids", it is meant herein amino acids that are individually present as unbound ingredients in a composition. Free amino acids do not form part or are not contained into peptides or proteins and are not joined to other amino acids by peptide bonds.

By the term "sulphur-containing free amino acids", it is meant herein free amino acids containing one or more atoms of sulphur selected from free cysteine, cystine, methionine, and also from sulphur sources such as i) homocysteine, cystathionine, and cysteamine; ii) short peptides such as glutathione and homoglutathione; and iii) thiamine.

By the term "total free amino acids", it is meant herein all the free amino acids contained in a product (in particular here, a PE). No distinction is made between any of the free amino acids that are contained in said product.

The term "yeast" herein refers to any yeast, preferably inactive, as well as to yeast by-products that are compatible with compositions for animal consumption. Yeasts are well known in the art as being protein-rich. Yeasts include, without limitation, brewer's yeast, baker's yeast, torula yeast, molasses yeast, ethanol yeasts, and the like. Yeast by-products include, without limitation, yeast extracts, yeast hydrolysates, yeast autolysates, cream yeasts, etc.

By the term "carbonyl composition", it is meant herein any material (, that can provide a free or available carbonyl group (such that the carbonyl group is available to react with an amino reactant in a Maillard reaction), with the proviso that it comprises more than 20% and up to 100% by weight of monosaccharides and/or disaccharides and/or oligosaccharides.

Preferably, a "carbonyl composition" of the present invention comprises from 21 to 100% by weight of monosaccharides and/or disaccharides and/or oligosaccharides. More preferably, it comprises from 23 to 100% by weight of monosaccharides and/or disaccharides and/or oligosaccharides. Yet more preferably, it comprises from 25 to 100% by weight of monosaccharides and/or disaccharides and/or oligosaccharides. Even yet more preferably, it comprises from 28% to 100% by weight of monosaccharides and/or disaccharides and/or oligosaccharides.

Examples of carbonyl compositions include, but are not limited to, monosaccharides, disaccharides, oligosaccharides, hydrolysis products thereof (i.e., hydrolysis products of disaccharides and/or of oligosaccharides); and materials containing carbonyl groups; all those compounds bearing at least one carbonyl group such as aldehydes, ketones, alpha-hydroxycarbonyl or dicarbonyl compounds; and with the proviso that they comprise more than 20% and up to 100%, preferably from 21 to 100%, more preferably from 23 to 100%, yet more preferably from 25 to 100%, and even yet more preferably from 28 to 100% by weight of monosaccharides and/or disaccharides and/or oligosaccharides.

Non-limiting examples of monosaccharides are xylose, arabinose, ribose, glucose, fructose, mannose, galactose, rhamnose, fucose, glyceraldehyde, dihydroxyacetone, erythrulose, erythrose, threose, ribulose, xylulose, lyxose, and the like.

Non-limiting examples of disaccharides are lactose and maltose.

By the term "oligosaccharide", it is meant herein a small saccharide polymer (typically, a polymer having from 3 to 10 simple sugars or monosaccharides), whereas a "polysaccharide" is herein a larger saccharide polymer than an oligosaccharide (typically a polymer having more than 10 monosaccharides).

Non-limiting examples of oligosaccharides are trioses such as raffinose and tetraoses such as stachyose.

Non-limiting examples of materials containing carbonyl groups are glucose syrups, fructose syrups, caramel, and molasses.

A requirement in the context of the present invention is that the carbonyl composition under consideration comprises more than 20% and up to 100%, preferably from 21 to 100%, more preferably from 23 to 100%, yet more preferably from 25 to 100%, and even yet more preferably from 28 to 100% by weight of monosaccharides and/or disaccharides and/or oligosaccharides.

The term "inorganic phosphate compound" as used herein means a chemical compound comprising at least one phosphorus atom. This chemical compound may be natural or synthetic, ionized or not. Examples of inorganic phosphate compounds include polyphosphates, pyrophosphates, and monophosphates.

"Inorganic pyrophosphates" or "pyrophosphates" include alkali metal pyrophosphates, encompassing monoalkali metal pyrophosphates and polyalkali metal pyrophosphates.

Examples of pyrophosphates include, without limitation, tetrahydrogen pyrophosphate, sodium trihydrogen pyrophosphate, potassium trihydrogen pyrophosphate, disodium dihydrogen pyrophosphate, dipotassium dihydrogen pyrophosphate, dicalcium pyrophate, monocalcium dihydrogen pyrophosphate, trisodium hydrogen pyrophosphate, tripotassium hydrogen pyrophosphate, tetrasodium pyrophosphate, tetrapotassium pyrophosphate, and tetraferric pyrophosphate.

Non-limiting examples of polyphosphates are tripolyphosphates (such as sodium tripolyphosphate, potassium tripolyphosphate), pentapolyphosphates, and hexapolyphosphates (such as sodium hexametaphosphate)

Examples of monophosphates include, without limitation, monosodium monophosphate, disodium monophosphate, trisodium monophosphate, monopotassium monophosphate, dipotassium monophosphate, tripotassium monophosphate, monocalcium monophosphate, dicalcium phosphate, tricalcium phosphate, and monoferric monophosphate.

The term "animal digest" means herein material which results from chemical and/or enzymatic hydrolysis of clean, undecomposed animal tissue. In some embodiments, an animal digest as used herein is fully consistent with the definition promulgated by the Association Of American Feed Control Officials, Inc. (AAFCO). Animal digest is preferably derived from animal tissues, including cold-blooded marine animals, excluding hair, horns, teeth, hooves, and feathers. The skilled artisan will appreciate that while such tissues are not preferred, trace amounts might be found unavoidably even under good manufacturing practices. Also not included are visceral contents or foreign or fecal matter, although trace contaminant amounts are sometimes present. An animal digest may be dried or not. Examples of animal digests are:

digest of poultry (or pork, beef, sheep, lamb, fish, etc): material from poultry (pork, beef, etc) which results from chemical and/or enzymatic hydrolysis of clean and undecomposed tissue;

digest of pork (or beef, sheep, lamb, fish, etc) by-products: material from pork (beef, etc.) which results from chemical and/or enzymatic hydrolysis of clean and undecomposed tissue from non-rendered clean parts from cattle (pigs, sheep, lamb, etc), other than meat, for example lungs, spleen, kidneys, brain, livers, blood, partially-defatted low-temperature fatty tissue, and stomachs and intestines, freed of their contents;

digest of poultry by-products: material which results from chemical and/or enzymatic hydrolysis of clean and undecomposed tissue from non-rendered clean parts of poultry, other than meat, such as livers, hearts, heads, feet, and viscera. As used herein, "poultry" encompasses any species or kind of bird, preferably chicken, turkey, duck, and the like; and digest of fish by-products: material which results from chemical and/or enzymatic hydrolysis of clean and undecomposed tissue from non-rendered clean parts from fish, other than meat. As used herein, "fish" encompasses any species or kind of fish or crustaceans, preferably tuna, salmon, cod, whitefish, shrimp, sardine, and the like.

Animal digests may also be referred to as "animal products" or "animal by-products", all these terms being used herein as synonymous.

As used herein, a "cat food ingredient" is any compound, composition or material that is suitable for cat consumption. Non-limiting examples of cat food ingredients are PEs, PECs, animal digests, proteins, peptides, amino acids, grains, carbohydrates, fats or lipids, nutrients, anti-oxidants, preservatives, surfactants, texturing agents, colouring agents, flavours, inorganic phosphate compounds, etc.

As used herein, a "palatability-enhancing ingredient" is any compound, composition or material that is suitable for cat consumption and that has a food palatability-enhancing effect. Non-limiting examples of palatability-enhancing ingredients are animal digests, yeasts, proteins, peptides, amino acids, carbohydrates, fats or lipids, nutrients, anti-oxidants, preservatives, surfactants, texturing agents, flavours, inorganic phosphate compounds, etc. Ingredients may be comprised as such in a PEC, or they can be incorporated into the PEC and react in situ for producing transformed materials that are also encompassed by the term "palatability-enhancing ingredients".

"Proteins" include all conventional protein sources that are compatible for animal (in particular, cat) consumption, especially plant or vegetable proteins, animal proteins (such as casein or albumin or animal digests), and microbial proteins (e.g., yeast).

Examples of vegetable proteins are corn gluten, soy protein, soy flour, hydrolyzed vegetable protein (HVP), and the like.

Examples of grains are corn, milo, alfalfa, wheat, barley, rice, soy, and the like.

Examples of carbohydrates include dextrose, fructose, sucrose, fibers, starches, and the like.

Examples of fats include tallow, oils (from any origin such as animal, fish, vegetable, dairy oils).

Examples of nutrients include, without limitation, vitamins, minerals and electrolytes, such as vitamins A, C, E, B12, D3, folic acid, D-biotin, cyanocobalamin, niacinamide, thiamine, riboflavin, pyridoxine, menadione, beta-carotene, calcium pantothenate, choline, inositol, calcium, potassium, sodium, zinc, iron, manganese, copper, iodine, and the like.

Anti-oxidants and preservatives are, for example, tocopherols, rosemary extract, potassium sorbate, sorbic acid, and the like.

A "thermal reaction" is, according to the present invention, a reaction triggered by a "thermal treatment", i.e., a reaction obtained by combining at an elevated temperature, at least one carbonyl compound and at least one amino reactant. Such a reaction may actually include various concomitant and/or successive reactions, including, e.g., Maillard reaction(s). Such thermal reactions are well known by the person skilled in the art. It is commonly referred to the "Maillard reaction" for designating a non-enzymatic browning involving in fact a series of thermal reactions between reducing sugars and amino acids. Thus, with this enlarged meaning, the "Maillard reaction" is equivalent to the "thermal reaction".

It is thus meant herein by the term "Maillard ingredient(s)", one or more carbonyl compound and/or one or more amino reactant. Indeed, Maillard ingredients are ingredients used to achieve one or more thermal reactions as defined above.

The term "carrier" means a usually inactive substance that is used in association with an active compound or mix of compounds. Under these circumstances, a "carrier" typically aids the application of said active compound or mix of compounds.

Alternatively, the term "carrier" can be equivalent to the term "filler" which refers to a substance added to a composition to increase weight and/or size and/or bulk thereof, or to fill space in a composition.

Yet alternatively, the term "carrier" can refer to a "carrier for concentrating" or "carrier for drying", encompassing conventional compounds that are well-known in the art to perform a concentration or a drying step in a given method. Examples of "carriers for concentrating" or "carriers for drying" are microbial proteins (e.g., yeasts), animal proteins, vegetable proteins, carbohydrates (e.g., maltodextrin, cyclodextrin), as well as minerals or inorganic compounds, including inorganic phosphate compounds.

Of course, the exact meaning of the term "carrier" when used herein will be clear to the skilled artisan based on the context and in light of his general knowledge in the art.

As used herein, the term "aqueous medium" means a solution in which the solvent is water and that contains solid or liquid ingredient miscible with water or that has the capacity to dissolve in water at ambient temperature.

"Coating", as used herein, refers to the topical deposition of the PE or PEC onto the surface of the basal food composition, such as by spraying, dusting, and the like.

"Inclusion" as used herein, refers to the addition of the PE or PEC internally to the cat food preparation, by mixing it with other cat food ingredients, before further processing steps for obtaining the final cat food product (including thermal treatment and/or extrusion and/or retorting, etc.).

The term "single package" means that the components of a kit are physically associated in or with one or more containers and considered a unit for manufacture, distribution, sale, or use. Containers include, but are not limited to, bags, boxes, cartons, bottles, packages of any type or design or material, over-wrap, shrink-wrap, stapled or otherwise affixed components, or combinations thereof. A single package may be containers of individual components physically associated such that they are considered a unit for manufacture, distribution, sale, or use.

As used herein, "means for communicating information or instructions" is a kit component under any form suitable for providing information, instructions, recommendations, and/or warranties, etc. Such a means can comprise a document, digital storage media, optical storage media, audio presentation, visual display containing information. The means of communication can be a displayed web site, brochure, product label, package insert, advertisement, visual display, etc.

DESCRIPTION OF THE INVENTION

A first aspect of the present invention relates to a non-fatty PE for use in cat food comprising:
at least one amino reactant characterized by a ratio AAS/AAT of sulfur-containing free amino acids (AAS) to total free amino acids (AAT) from 1 to 12.8% by weight; and
at least one carbonyl composition comprising more than 20% and up to 100% by weight of monosaccharides and/or disaccharides and/or oligosaccharides.

Preferably, said ratio AAS/AAT is equal or superior to about 2% by weight, yet preferably equal or superior to about 2.50% by weight, and even yet preferably equal or superior to about 2.73% by weight.

Preferably, said ratio AAS/AAT is in the range 2.00-12.80% by weight, yet preferably in the range 2.50-12.80% by weight, and even yet preferably in the range 2.73-12.80% by weight.

Preferably, said carbonyl composition comprises from 21 to 100%, more preferably from 23 to 100%, yet more preferably from 25 to 100%, and even yet more preferably from 28 to 100% by weight of monosaccharides and/or disaccharides and/or oligosaccharides.

Preferably, said PE is obtained upon thermally treating said at least one amino reactant and said at least one carbonyl composition. If so, the thermal treatment comprises heating said at least one amino reactant and said at least one carbonyl composition at a temperature ranging from about 80° C. to about 200° C. for a period of time ranging from about 10 sec to about 210 min.

In particular, said temperature can range from about 85° C. to about 190° C., preferably from about 90° C. to about 180° C., yet preferably from about 95° C. to about 170° C.

Yet in particular, said period of time can range from about 15 sec to about 150 min, preferably from about 1 min to about 120 min, yet preferably from about 3 min to about 100 min, even yet preferably from about 5 min to about 80 min.

Preferably, said thermal treatment comprises heating said at least one amino reactant and said at least one carbonyl composition at a temperature ranging from about 95° C. to about 170° C. for a period of time ranging from about 5 min to about 80 min.

In practice, depending upon the duration of the thermal treatment, the skilled artisan will be able to select, in light of his general knowledge in the art, an appropriate method among standard methods for heating food compositions such as batch cooking, semi-continuous cooking, continuous cooking, and the like.

Preferably, said amino reactant is selected from amino acids, hydrolysates and extracts of peptides (including dipeptides, tripeptides, and oligopeptides) and proteins, hydrolysed vegetable protein (HVPs), peptones, yeast extracts, yeast hydrolysates, yeast autolysates, cream yeasts, soy sauces, and combinations thereof.

Said carbonyl composition is preferably selected from the group consisting of monosaccharides, disaccharides, oligosaccharides; and materials containing carbonyl groups such as glucose syrups, fructose syrups, caramel, and molasses; and combinations thereof, with the proviso that they comprise more than 20% up to 100%, preferably from 21 to 100%, more preferably from 23 to 100%, yet more preferably from 25 to 100%, and even yet more preferably from 28 to 100% by weight of monosaccharides and/or disaccharides and/or oligosaccharides.

Said amino reactant is preferably present in the PE in an amount of about 0.5 to 95%, yet preferably about 0.75 to 80%, more preferably about 1 to 65%, yet more preferably about 1.25 to 50%, and even more preferably about 1.5 to 35%, by weight of the PE.

Said carbonyl composition is preferably present in the PE in an amount of about 0.5 to 99%, yet preferably about 1 to 95%, more preferably about 1.5 to 90%, yet more preferably about 2 to 85%, and even more preferably about 2.5 to 80%, by weight of the PE.

The PE can be dry or liquid.

As being non-fatty, the PE according to the present invention does not contain any structured lipid phase.

Another aspect of the present invention concerns a PEC for use in cat food comprising at least one PE as described herein, in mixture with one or more palatability-enhancing ingredients.

Said PE is preferably present in the PEC in an amount of about 0.1 to 99.9%, yet preferably about 0.25 to 95%, more preferably about 0.5 to 90%, yet more preferably about 1 to 85%, and even more preferably about 1.5 to 80%, by weight of the composition.

Preferably, said palatability-enhancing ingredients are selected from inorganic phosphate compounds, animal digests, yeasts, and combinations thereof. Yet preferably, said palatability-enhancing ingredients comprise at least one inorganic phosphate compound and at least one animal digest.

Said inorganic phosphate compounds are preferably selected from the group consisting of phosphoric acid, pyrophosphates, monophosphates, polyphosphates, and combinations thereof.

A preferred inorganic phosphate compound according to the present invention is a pyrophosphate compound selected from disodium pyrophosphate, trisodium pyrophosphate, tetrasodium pyrophosphate, dipotassium pyrophosphate, tripotassium pyrophosphate, tetrapotassium pyrophosphate, tetraferric pyrophosphate, and combinations thereof. A more particularly preferred pyrophosphate compound is trisodium pyrophosphate.

A preferred polyphosphate compound for use in the present invention is sodium tripolyphosphate.

Said inorganic phosphate compound is preferably present in the PEC in an amount of about 0.01 to 75%, yet preferably about 0.05 to 70%, more preferably about 0.1 to 65%, yet more preferably about 0.25 to 60%, and even more preferably about 0.5 to 55%, by weight of the composition.

Preferred animal digests are poultry product or by-product digests, pork product or by-product digests, and fish by-product digests, and combinations thereof.

Said animal digest is preferably present in said PEC in an amount of about 0.01 to 99%, more preferably about 0.05 to 95%, yet more preferably about 0.1 to 90%, even more preferably about 0.2 to 85%, and yet even more preferably about 0.5 to 80% by weight of the composition.

Preferred yeasts for use in the present invention are brewer's yeast, molasses yeast, and by-products thereof.

The yeast content in said PEC is preferably of about 0.01 to 99%, yet preferably about 0.05 to 95%, more preferably about 0.1 to 90%, yet more preferably about 0.2 to 85%, and even more preferably about 0.5 to 80%, by weight of the composition.

Advantageously, the PEC comprises one or more other palatability-enhancing ingredients as defined above.

The content of such ingredients in said PEC is preferably of about 0.01 to 99%, yet preferably about 0.05 to 95%, more preferably about 0.1 to 90%, yet more preferably about 0.2 to 85%, and even more preferably about 0.5 to 80%, by weight of the composition.

The PEC can be dry or liquid.

A further aspect of the present invention is related to a method for preparing a non-fatty PE for use in cat food comprising:
a) mixing in an aqueous medium at least one amino reactant characterized by a ratio AAS/AAT from 1 to 12.8% by weight, and at least one carbonyl composition comprising more than 20% and up to 100% by weight of monosaccharides and/or disaccharides and/or oligosaccharides;
b) optionally, thermally treating the thus obtained mixture;
c) optionally, drying the resulting mixture; and
d) obtaining said PE.

Preferably, said carbonyl composition comprises from 21 to 100%, more preferably from 23 to 100%, yet more preferably from 25 to 100%, and even yet more preferably from 28 to 100% by weight of monosaccharides and/or disaccharides and/or oligosaccharides.

Preferably, said step b) comprises heating said at least one amino reactant and said at least one carbonyl composition at a temperature ranging from about 80 to about 200° C. for a period of time ranging from about 10 sec to about 210 min.

In particular, said temperature can range from about 85° C. to about 190° C., preferably from about 90 to about 180° C., yet preferably from about 95 to about 170° C.

Yet in particular, said period of time can range from about 15 sec to about 150 min, preferably from about 1 min to about 120 min, yet preferably from about 3 min to about 100 min, even yet preferably from about 5 min to 80 min.

Preferably, said thermal treatment comprises heating said at least one amino reactant and said at least one carbonyl composition at a temperature ranging from about 95° C. to about 170° C. for a period of time ranging from about 5 min to about 80 min.

As yet mentioned above, in practice, depending upon the duration of the thermal treatment, the skilled artisan will be able to select, in light of his general knowledge in the art, an appropriate method among standard methods for heating food compositions such as batch cooking, semi-continuous cooking, continuous cooking, and the like.

In particular, said drying of step c) is performed so as to remove any excess water. In particular, the resulting water content is less than or equal to about 10%, preferably from about 1 to about 8%, by weight of the thus obtained product. For example, a dry product can be obtained by combining the product to be dried with carriers as defined above in appropriate proportions, and by blending the components. The mixture is then dried by evaporation at an appropriate temperature, and a dry product is obtained.

A non-fatty PE for use in cat food that is obtainable by a method as described above is also an aspect of the present invention.

Another aspect of the present invention concerns a method for preparing a PEC for use in cat food comprising:
a) providing at least one PE as described herein;
b) mixing said at least one PE with one or more palatability-enhancing ingredients;
c) optionally, drying the thus obtained mixture; and
d) obtaining said PEC.

Preferably, said at least one PE of step a) is prepared by a method as described above.

Preferably, the method for preparing a PEC further comprises, after said step a), a step a1) of drying said at least one PE.

In particular, said drying of step c) and/or of step a1) is performed so as to remove any excess water. In particular, the resulting water content is less than or equal to about 10%, preferably from about 1 to about 8%, by weight of the thus obtained product. For example, a dry product is obtained by combining the product to be dried with carriers as defined above in appropriate proportions, and by blending the components. The mixture is then dried by evaporation at an appropriate temperature, and a dry product is obtained.

A PEC for use in cat food that is obtainable by a method as described above is also an aspect of the present invention.

A typical example of a method for preparing a liquid animal digest for use in the production of a PEC is as follows. Liquid ingredients are combined in a mixer. Wet ingredients are ground or emulsified to a slurry and the liquid ingredients are combined therewith. If need be, a commercially available protease may be added to the slurry to hydrolyze proteins, and later inactivated with heat, acid or another method. Preservatives such as sorbic acid can also be added. Water is added to adjust the viscosity and the solids content of the slurry to facilitate spray application.

It is further disclosed herein a cat food having enhanced palatability that comprises at least one PE and/or at least one PEC as described herein.

Yet another aspect of the present invention is related to a method for enhancing the palatability of a cat food or, in other words, for producing a cat food having enhanced palatability comprising:

a) adding to a cat food preparation, at least one PE and/or at least one PEC as described herein; and
b) obtaining a cat food having enhanced palatability.

A cat food having enhanced palatability that is obtainable by a method as described above is also disclosed herein.

Typically, dry cat foods such as kibbles can be prepared by different common methods. One of these methods, that is widely used, is a cooker-extruder method. In the cooker-extruder method, ingredients are first blended together to form an admixture. This admixture is transferred into a steam conditioner where it is sufficiently moistened to become extrudable. The admixture then enters a cooker-extruder where it is cooked at an elevated temperature and pressure and then forced out of the apparatus through a die. This die forms the extruder product into a specific shape. Individual pieces of food are created by periodically slicing off the end of the extruded stream of product. The individual pieces are then dried in a hot air dryer. Generally, the product is dried until it contains less than 14% moisture, and preferably about 5 to 10% moisture. The dried particles or pieces are then transferred by bulk conveyor to a coating drum and sprayed with fat. Other liquids, such as, for example, phosphoric acid may alternatively be applied to the pieces, or applied in addition to the fat. The resulting pellets or kibbles constitute the basal cat food preparation, the palatability of which will be enhanced using the PEs and/or PECs described herein.

Moist cat foods that are gravy-based or jelly-based can be prepared by grinding meat, meat mimetics, meat by-products, carbohydrates and/or grains, texturing agents, and forming the ground mixture via low pressure extrusion, then cooking through a steaming tunnel. At the tunnel outlet, the mixture is cut into pieces. The gravy- or jelly-type matrix is added to the resulting pieces, then sealed in cans or pouches and retorted, so as to obtain chunks-in gravy or chunks-in jelly food products.

Moist cat foods that are not gravy-based or jelly-based can be prepared by grinding meat, meat mimetics, meat by-products, carbohydrates and/or grains, and mixing with water and texturing agents. Then, the overall mixture is sealed in cans and retorted, so as to obtain loaves.

The addition step a) mentioned above can thus be performed, depending on the cat food and PE or PEC, either by incorporating or including said PE or PEC into the cat food preparation, or by coating said cat food preparation with said PE or PEC.

For example, one can cite a method for coating dry cat foods such as kibbles. Kibbles of uncoated, extruded basal cat food can be placed in a container such a tub or a coating drum for mixing. A fat, such as pork fat or poultry fat, is heated and then sprayed onto the cat food in a manner to obtain a coating of the kibbles. The coating need not be a continuous layer, but preferably is uniform. After the fat, a PE or PEC may be applied as either a liquid or a dry powder, while the product is mixed. A liquid PE or PEC is typically sprayed on while a dry PE or PEC is typically dusted on. Alternatively, PEs or PECs can be mixed with the fat and applied concurrently. Yet alternatively, PEs or PECs are coated before deposition of fat.

Alternatively, the PE or PEC can be incorporated or included into the cat food preparation according to the following method. The PE or PEC is contacted with the raw ingredients of the cat food preparation prior to cooking. In this case, the PE or PEC is combined to proteins, fibre, carbohydrates and/or starch, etc., of the basal cat food preparation and is cooked with those materials in the cooker-extruder.

Inclusion into moist cat foods can be achieved as follows. The liquid or dry PE or PEC can be applied in a gravy- or jelly-type matrix during the blending process in addition to the other cat food ingredients. The liquid or dry PE or PEC can also be applied into a meat-by mixtures for chunks or loaf preparation. In this case, it can be added to raw materials before or after the grinding process. The meat-by mixture may be cooked in a steam or grilling oven in the case of chunks manufacturing, or directly sealed in cans in the case of loaf manufacturing.

PEs and PECs are generally useful in cat foods such as nutritionally-balanced mixtures containing appropriate cat food ingredients including proteins, fibre, carbohydrates and/or starch, etc. Such mixtures are well known to those skilled in the art, and their composition depends on many factors such as, for example, the desired food balance for the specific type of cat. Additional cat food ingredients may include vitamins, minerals, seasonings, preservatives, and surfactants. The food balance, including the relative proportions of vitamins, minerals, lipids, proteins and carbohydrates, is determined according to the known dietary standards in the veterinary field, for example by following recommendations of the National Research council (NRC), or the guidelines of the American Association of Feed Control Officials (AAFCO).

Preferably, the herein-disclosed cat food is selected from wet nutritionally-balanced cat foods, dry nutritionally-balanced cat foods, semi-moist nutritionally-balanced cat foods, supplements, treats, and toys.

Wet nutritionally-balanced cat foods are preferably selected from the group consisting of: chunks-in-jelly food products, chunks-in-gravy food products, loafs, and soups.

Dry nutritionally-balanced cat foods are preferably kibbles.

Yet another part of the present disclosure is directed to a method for feeding cats comprising at least:

a) providing a cat food as described herein; and
b) feeding said cat food to cats.

A further aspect of the present invention concerns a kit for enhancing palatability of a cat food comprising at least the following components, in one or more containers in a single package:

a) at least one PE as described herein; and/or
b) at least one PEC as described herein; and
c) optionally, at least one palatability-enhancing ingredient; and
d) optionally, at least one cat food ingredient; and
e) optionally, means for communicating information about or instructions for using said components.

The above-described PEs and PECs provide significant advantages over the prior art. The effects of the present invention can be measured by a test that is commonly called "two-bowl test" or "versus test". Of course, the person skilled in the art is free to use any other appropriate test than the two bowl test herein described to determine preference. Such alternative tests are well known in the art.

Principle of the Two-Bowl Test:

The test is based on the postulate whereby the more food consumed, the more palatable it is.

Individual versus (Two bowls) appetence tests, based on the comparison between two foods, were carried out. Tests are performed either on panel of cats.

Operating Method of the Test:

Identical amounts of food A and food B were weighed out and placed in identical bowls. The amount present in each ration enables the daily requirements to be met.

Distribution of the bowls:

The bowls were presented at the same time to each cat in an individual loose box and their positions were switched at each meal to avoid a choice led by handedness.

Duration of the test:

Cat test for dry food: from about 10 minutes to about 20 hours;

Cat test for wet food: from about 5 minutes to about 16 hours;

Parameters tudied:

Measured parameters: First food consumed ("initial appeal") and amount of each food consumed by the end of the test;

Calculated parameters: individual consumption ratio in % (CR)

$$CR_A = \text{consumption of } A(g) \times 100 / (\text{consumption of } A+B) \, (g)$$

$$CR_B = \text{consumption of } B(g) \times 100 / (\text{consumption of } A+B) \, (g);$$

Average consumption ratio (ACR)=average of all individual ratios (an equal importance is given to each cat, regardless of its size and of its corresponding consumption).

If cats have higher or lower consumption compared to predetermined values (which are function of, e.g., the cat weight and/or metabolism), they are not taken into account into statistical treatment.

Statistical Analysis:

Statistical analysis was used to determine if there was a significant difference between the 2 ratios. A Student's t-test with 3 error thresholds, namely 5%, 1% and 0.1%, was performed.

Significance levels are noted as below:

| | |
|---|---|
| NS not significant | ($p > 0.05$) |
| * significant | ($p \leq 0.05$) |
| ** highly significant | ($p \leq 0.01$) |
| *** very highly significant | ($p \leq 0.001$) |

The present invention will be further described by reference to the following examples, which are presented for the purpose of illustration only and are not intended to limit the scope of the invention.

EXAMPLES

The Examples below report assessment of the palatability-enhancing effect of:

liquid PECs including liquid PEs characterized by their ratio AAS/AAT: Example 1;

dry PECs including dry PEs characterized by their ratio AAS/AAT: Example 2;

liquid PECs including liquid PEs characterized by their ratio AAS/AAT and by their carbonyl compound profile: Example 3;

liquid PECs including liquid PEs characterized by their ratio AAS/AAT and prepared by a method including or not a thermal treatment: Example 4.1;

liquid PECs including liquid PEs characterized by their ratio AAS/AAT and prepared by a method including variations of the thermal treatment conditions: Example 4.2;

liquid PECs having different animal digest contents and including liquid PEs characterized by their ratio AAS/AAT: Example 5;

liquid PEC applied at different levels on experimental foods and including a PE characterized by its ratio AAS/AAT: Example 6;

dry PE characterized by its ratio AAS/AAT and applied by inclusion in a diet: Example 7.

Example 1: Assessment of the Palatability-Enhancing Effect of Liquid PECs Including Liquid PEs Characterized by Their Ratio AAS/AAT 1.1. In this Example, 8 liquid PEs characterized by different AAS/AAT ratio values were prepared.

The formulations of PEs 1, 2, 3, 4, 5, 6, 7, and 8 are described in Table 1 below wherein percentages are expressed by weight of the PEs.

TABLE 1

| Formulation of PE | PE 1 | PE 2 | PE 3 | PE 4 | PE 5 | PE 6 | PE 7 | PE 8 |
|---|---|---|---|---|---|---|---|---|
| Free amino acid mixture 1 | 17.23 | 17.23 | 17.23 | 17.23 | | | | |
| Free amino acid mixture 2 | | | | | 18.32 | | | |
| Free amino acid mixture 3 | | | | | | 17.00 | | |
| Free amino acid mixture 4 | | | | | | | 19.31 | |
| Free amino acid mixture 5 | | | | | | | | 16.22 |
| Carbonyl compound 1 = monosaccharide a | | | 15.07 | | | 15.07 | 15.07 | 15.07 |
| Carbonyl compound 2 = material containing carbonyl groups * | 62.5 | 62.5 | | 75 | 75 | | | |

TABLE 1-continued

| Formulation of PE | PE 1 | PE 2 | PE 3 | PE 4 | PE 5 | PE 6 | PE 7 | PE 8 |
|---|---|---|---|---|---|---|---|---|
| Water | | | 38.24 | | | 38.24 | 38.24 | 38.24 |
| Carrier (Maltodextrine) | 20.27 | 20.27 | 29.46 | 7.77 | 6.68 | 29.69 | 27.38 | 30.47 |
| AAS/AAT ratio | 3.16% | 3.16% | 3.16% | 3.16% | 8.90% | 12.80% | 14.01% | 46.62% |

* Carbonyl compound 2: contained minimum 25% of mono- and/or disaccharides and/or oligosaccharides.

The formulations of free amino acid mixtures 1, 2, 3, 4 and 5 are described in Table 2 below wherein the percentages are expressed by weight in the free amino acid mixtures ("Mix").

TABLE 2

| Formulation of Free amino acid mixture | Mix 1 | Mix 2 | Mix 3 | Mix 4 | Mix 5 |
|---|---|---|---|---|---|
| % sulfur-containing free amino acids (Methionine-Cysteine-Cystine) in the mixture | 3.16 | 8.90 | 12.80 | 14.01 | 46.62 |
| % of non-sulfur free amino acids in the mixture (1) | 96.84 | 91.10 | 87.20 | 85.99 | 53.38 |

(1) Represents % of free amino acids without sulfur: glutamic acid, alanine, leucine, valine, lysine, arginine, serine, phenylalanine, aspartic acid, isoleucine, threonine, glycine, proline, histidine, tyrosine.

Liquid PEs 1, 2, 3, 4, 5, 6, 7 and 8 were prepared using the following methods.

The ingredients of PE 1, 2, 3, 4, 5, 6, 7 or 8 were mixed and the pH was adjusted to a value of 7.5 by addition of NaOH solution. The mixtures were heated at 120° C. during 20 minutes. Then, the temperature was cooled down at less than 40° C., thereby obtaining liquid PE 1, 2, 3, 4, 5, 6, 7 or 8.

The formulation of PE 2 is the same as that of PE 1, but the heating temperature used in the method for preparing PE 2 was 130° C. instead of 120° C. for preparing PE 2.

1.2. The formulations of liquid PECs 1, 2, 3, 4, 5, 6, 7, 8, 9 and 10 are described in Table 3 below wherein percentages are expressed by weight of the PECs.

TABLE 3

| Formulation of the PEC | PEC 1 | PEC 2 | PEC 3 | PEC 4 | PEC 5 | PEC 6 | PEC 7 | PEC 8 | PEC 9 | PEC 10 |
|---|---|---|---|---|---|---|---|---|---|---|
| PE 1 | 5% | | | | | | | | | |
| PE 2 | | | | | | | | 5% | | |
| PE 3 | | 5% | | | | | | | | |
| PE 4 | | | | | | | | 5% | | |
| PE 5 | | | 5% | | 5% | | | 5% | | |
| PE 6 | | | | 5% | | | | | 5% | |
| PE 7 | | | | | | | | | | 5% |
| PE 8 | | | | | 5% | | | | | |
| Liquid poultry digest «Dig 1»(2) | 95% | 95% | 95% | 95% | 95% | | | | | |
| Liquid pork digest «Dig 2» (2) | | | | | | 95% | 95% | 95% | 95% | 95% |

(2) The liquid poultry digest "Dig 1" of the commercial range SPF did not contain trisodium pyrophosphate. The liquid pork digest "Dig 2" of the commercial range SPF contained trisodium pyrophosphate.

1.3. The coating formulas of Experimental Diets ("Exp. Diets") 1, 2, 3, 4, 5, 6, 7, 8, 9, and 10 and Control Diets A, B and C are described in Table 4 below wherein percentages are expressed by weight of the Experimental Diets.

TABLE 4

| | Exp. Diet 1 | Exp. Diet 2 | Exp. Diet 3 | Exp. Diet 4 | Exp. Diet 5 | Exp. Diet 6 | Exp. Diet 7 | Exp. Diet 8 | Exp. Diet 9 | Exp. Diet 10 | Control Diet A | Control Diet B | Control Diet C |
|---|---|---|---|---|---|---|---|---|---|---|---|---|---|
| Poultry fat | 6% | 6% | 6% | 6% | 6% | 6% | 6% | 6% | 6% | 6% | 6% | 6% | 6% |
| PEC 1 | 3% | | | | | | | | | | | | |
| PEC 2 | | 3% | | | | | | | | | | | |
| PEC 3 | | | 3% | | | | | | | | | | |
| PEC 4 | | | | 3% | | | | | | | | | |
| PEC 5 | | | | | 3% | | | | | | | | |
| PEC 6 | | | | | | 2% | | | | | | | |
| PEC 7 | | | | | | | 2% | | | | | | |
| PEC 8 | | | | | | | | 2% | | | | | |
| PEC 9 | | | | | | | | | 2% | | | | |
| PEC 10 | | | | | | | | | | 2% | | | |

TABLE 4-continued

| | Exp. Diet 1 | Exp. Diet 2 | Exp. Diet 3 | Exp. Diet 4 | Exp. Diet 5 | Exp. Diet 6 | Exp. Diet 7 | Exp. Diet 8 | Exp. Diet 9 | Exp. Diet 10 | Control Diet A | Control Diet B | Control Diet C |
|---|---|---|---|---|---|---|---|---|---|---|---|---|---|
| Liquid poultry digest "Dig 1" | | | | | | | | | | | 3% | 3% | |
| Liquid pork digest "Dig 2" | | | | | | | | | | | | | 2% |
| Dry poultry digest "Dig 3" (3) | 0.75% | 0.75% | 0.75% | 0.75% | | | | | | | | 0.75% | |

(3) The dry poultry digest "Dig 3" of the commercial range SPF contained trisodium pyrophosphate.

1.4. Food palatability to cats was assessed to compare Experimental Diets to Control Diets and, more particularly, to compare Experimental Diet 4 coated with liquid PEC 4 including liquid PE 6 characterized by a ratio AAS/AAT of 12.80% to Experimental Diet 5 coated with liquid PEC 5 including liquid PE 8 characterized by a ratio AAS/AAT of 46.62%.

The palatability results are presented in Table 5 below.

TABLE 5

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| | | | Without trisodium pyrophosphate | | | | | |
| Day 1 | Control diet A | 0% | Experimental Diet 1 | 3.16% | 21 | 79 | *** | 36 |
| Day 2 | | | | | 26 | 74 | *** | 36 |
| | | | With trisodium pyrophosphate | | | | | |
| Day 1 | Control diet B | 0% | Experimental Diet 2 | 3.16% | 31 | 69 | *** | 40 |
| Day 2 | | | | | 37 | 63 | ** | 40 |
| Day 1 | Control diet B | 0% | Experimental Diet 3 | 8.90% | 34 | 66 | *** | 39 |
| Day 2 | | | | | 38 | 62 | *** | 39 |
| Day 1 | Experimental Diet 5 | 46.62% | Experimental Diet 4 | 12.80% | 41 | 59 | * | 40 |
| Day 2 | | | | | 42 | 58 | * | 40 |
| Day 1 | Control diet C | 0% | Experimental Diet 6 | 3.16% | 42 | 58 | * | 38 |
| Day 2 | | | | | 39 | 61 | ** | 38 |
| Day 1 | Control diet C | 0% | Experimental Diet 7 | 3.16% | 38 | 62 | ** | 40 |
| Day 2 | | | | | 38 | 62 | * | 40 |
| Day 1 | Control diet C | 0% | Experimental Diet 8 | 8.90% | 31 | 69 | *** | 40 |
| Day 2 | | | | | 34 | 66 | *** | 39 |
| Day 1 | Control diet C | 0% | Experimental Diet 9 | 12.80% | 43 | 57 | * | 32 |
| Day 2 | | | | | 35 | 65 | ** | 32 |
| Day 1 | Control diet C | 0% | Experimental Diet 10 | 14.01% | 44 | 56 | NS | 33 |
| Day 2 | | | | | 43 | 57 | NS | 34 |

% A: average consumption of Food A;
% B: average consumption of Food B.

These results show that Experimental Diets are preferred to Control Diets, demonstrating the higher palatability to cats of foods coated with liquid PECs including liquid PEs characterized by an AAS/AAT ratio ranging from less or equal to 12.80%, regardless the presence or the absence of inorganic phosphate compounds (here, trisodium pyrophosphate) in the PECs.

These results also show that Experimental Diet 4 has a higher palatability to cats than Experimental Diet 5, demonstrating the advantage of including a liquid PE having an AAS/AAT ratio value of less or equal to 12.8% in the liquid PEC used for coating cat food.

These results demonstrate that the advantage of including a liquid PE having an AAS/AAT ratio value of 12.8% that was preferred to the control (Experimental diet 9 vs Control C), which was not the case with a liquid PE having an AAS/AAT ratio value of 14.01% (Experimental diet 10 vs Control C).

Example 2: Assessment of the Palatability-Enhancing Effect of Dry PECs Including Dry PEs Characterized by Their Ratio AAS/AAT 2.1. In this Example, the palatability-enhancing effect of a dry PEC containing dry poultry digest of the SPF commercial range and different amounts of a dry PE was assessed.

Dry PE 9 comprised an amino reactant characterized by an AAS/AAT ratio of 3.60%.

The formulation of dry PE 9 is described in Table 6 below wherein percentages are expressed by weight of PE 9.

TABLE 6

| Formulation of PE | PE 9 |
|---|---|
| Baker's yeast extract | 37.5 |
| Carbonyl compound 2 *= material containing carbonyl groups | 62.5 |

*Carbonyl compound 2: contained minimum 25% of mono- and/or disaccharides and/or oligosaccharides Dry PE 9 was prepared using the following method.

The ingredients of PE 9 were mixed and the pH was adjusted to a value of 7.5 by addition of NaOH solution. The mixture was heated at 120° C. during 20 minutes. Then, the temperature was cooled down at less than 40° C. The resulting product was then spray-dried at an appropriate temperature. Dry PE 9 was thus obtained.

2.2. The formulations of dry PECs 11, 12, 13, and 14 are described in Table 7 below wherein percentages are expressed by weight of the PECs.

TABLE 7

| Formulation of PEC | PEC 11 | PEC 12 | PEC 13 | PEC 14 |
|---|---|---|---|---|
| PE 9 | 15% | 30% | 15% | 30% |
| Dry poultry digest "Dig 4" (4) | 85% | 70% | 48% | 33% |
| Trisodium pyrophosphate | | | 37% | 37% |

(4) The dry poultry digest "Dig 4" of the commercial range SPF did not contain trisodium pyrophosphate 2.3. The coating formulas of Experimental Diets 11, 12, 13, and 14 and Control Diets D and E are described in Table 8 below wherein percentages are expressed by weight of the Experimental Diets.

TABLE 8

| Formulation of Diets | Exp. Diet 11 | Exp. Diet 12 | Exp. Diet 13 | Exp. Diet 14 | Control Diet D | Control Diet E |
|---|---|---|---|---|---|---|
| Poultry fat | 6% | 6% | 6% | 6% | 6% | 6% |
| PEC 11 | 1.5% | | | | | |
| PEC 12 | | 1.5% | | | | |
| PEC 13 | | | 2.0% | | | |
| PEC 14 | | | | 2.0% | | |
| Dry poultry digest « Dig 4 » | | | | | 1.5% | 1.3% |
| Trisodium pyrophosphate | | | | | | 0.7% |

2.4. Palatability results are presented in Table 9 below.

TABLE 9

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| Without trisodium pyrophosphate | | | | | | | | |
| Day 1 | Control | 0% | Experimental Diet 11 | 3.60% | 33 | 67 | *** | 33 |
| Day 2 | Diet D | | | | 40 | 60 | * | 34 |
| Day 1 | Control | 0% | Experimental Diet 12 | 3.60% | 30 | 70 | *** | 33 |
| Day 2 | Diet D | | | | 32 | 68 | *** | 35 |
| With trisodium pyrophosphate | | | | | | | | |
| Day 1 | Control | 0% | Experimental Diet 13 | 3.60% | 44 | 56 | NS | 37 |
| Day 2 | Diet E | | | | 41 | 59 | ** | 37 |
| Day 1 | Control | 0% | Experimental Diet 14 | 3.60% | 40 | 60 | * | 35 |
| Day 2 | Diet E | | | | 41 | 59 | * | 34 |

% A: average consumption of Food A;
% B: average consumption of Food B.

As shown in Table 9, food consumptions are significantly different between Control Diets and Experimental Diets, demonstrating the higher palatability to cats of Experimental Diets coated with dry PECs including dry PEs having a ratio AAS/AAT of less or equal to 12.80%, regardless the presence or the absence of inorganic phosphate compounds (here, trisodium pyrophosphate) in the PECs.

Example 3: Assessment of the Palatability-Enhancing Effect of Liquid PECs Including Liquid PEs Characterized by Their Ratio AAS/AAT and by Their Carbonyl Compound Profile 3.1. In this Example, 3 liquid PEs containing different types and amounts of carbonyl compounds were prepared.

Liquid PEs 10, 11, and 12 comprised an amino reactant having an AAS/AAT ratio of 3.60%.

The formulations of liquid PEs 10, 11, and 12 are described in Table 10 below wherein percentages are expressed by weight of the PEs.

TABLE 10

| Formulation of PE | PE 10 | PE 11 | PE 12 |
|---|---|---|---|
| Baker's yeast extract | 37.5 | 37.5 | 37.5 |
| Carbonyl compound 1 = Monosaccharide a | 12.5 | | 15.5 |
| Carbonyl compound 3 = Monosaccharide b | | 31.0 | |
| Carbonyl compound 4 = Disaccharide | | | 15.5 |
| Water | 31.0 | 31.5 | 31.5 |
| Carrier (Maltodextrine) | 19.0 | | |

Liquid PEs 10, 11, and 12 were prepared using the following method.

The ingredients of PE 10, 11, or 12 were mixed and the pH was adjusted to a value of 7.5 by addition of NaOH solution. The mixtures were heated at 120° C. during 20 minutes. Then, the temperature was cooled down at less than 40° C., thereby obtaining liquid PE 10, 11, or 12.

3.2. The formulations of liquid PECs 15, 16, and 17 are described in Table 11 below wherein percentages are expressed by weight of the PECs.

TABLE 11

| Formulation of PEC | PEC 15 | PEC 16 | PEC 17 |
|---|---|---|---|
| PE 10 | 5% | | |
| PE 11 | | 5% | |
| PE 12 | | | 5% |
| Liquid pork digest « Dig 2 » (6) | 95% | 95% | 95% |

(6) The liquid pork digest "Dig 2" of the commercial range SPF contained trisodium pyrophosphate.

3.3. The coating formulas of Experimental Diets 15, 16, and 17 and Control Diet C are described in Table 12 below wherein percentages are expressed by weight of the Experimental Diets.

TABLE 12

| Formulation of Diets | Exp. Diet 15 | Exp. Diet 16 | Exp. Diet 17 | Control Diet C |
|---|---|---|---|---|
| Poultry fat | 6% | 6% | 6% | 6% |
| PEC 15 | 2% | | | |
| PEC 16 | | 2% | | |
| PEC 17 | | | 2% | |
| Liquid pork digest « Dig 2 » | | | | 2% |

3.4. As show in Table 13 below, food consumptions are significantly different between Control Diet and Experimental Diets, demonstrating the higher palatability to cats of Experimental Diets coated with liquid PECs including liquid PEs having a ratio AAS/AAT of less or equal to 12.80% and characterized by different carbonyl compound profiles.

TABLE 13

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| Day 1 | Control | 0% | Experimental | 3.60% | 29 | 71 | *** | 40 |
| Day 2 | Diet C | | Diet 15 | | 32 | 68 | *** | 40 |
| Day 1 | Control | 0% | Experimental | 3.60% | 34 | 66 | *** | 40 |
| Day 2 | Diet C | | Diet 16 | | 41 | 59 | * | 39 |
| Day 1 | Control | 0% | Experimental | 3.60% | 47 | 53 | NS | 39 |
| Day 2 | Diet C | | Diet 17 | | 42 | 58 | * | 40 |

% A: average consumption of Food A;
% B: average consumption of Food B.

Example 4.1: Assessment of the Palatability-Enhancing Effect of Liquid PECs Including Liquid PEs Characterized by Their Ratio AAS/AAT and Prepared by a Method Including or not a Thermal Treatment 4.1.1. In this Example, 2 liquid PEs were prepared by a method comprising or not a thermal treatment.

Liquid PE 13 and PE 14 comprised an amino reactant characterized by an AAS/AAT ratio of 3.60%.

The formulations of liquid PEs 13 and 14 are described in Table 14 below.

TABLE 14

| Formulation of PE | PE 13 and PE 14 |
|---|---|
| Baker's yeast extract | 37.50 |
| Carbonyl compound 2* = material containing carbonyl groups | 62.5 |

*Carbonyl compound 2: contained minimum 25% of mono- and/or disaccharides and/or oligosaccharides The ingredients of PE 13 were mixed and the pH was adjusted to a value of 7.5 by addition of NaOH solution. The mixtures were heated at 120° C. during 20 minutes. Then, the temperature was cooled down at less than 40° C., thereby obtaining liquid PE 13.

Liquid PE 14 had the same formulation as liquid PE 13 but it was prepared using a method that did not comprise any thermal treatment. The ingredients of PE 14 were only mixed.

4.1.2. The formulations of liquid PECs 18 and 19 are described in Table 15 below wherein percentages are expressed by weight of the PECs.

TABLE 15

| Formulation of PEC | PEC 18 | PEC 19 |
|---|---|---|
| PE 13 | 5% | |
| PE 14 | | 5% |
| Liquid Poultry digest « Dig 1 » (7) | 95% | 95% |

(7) The liquid poultry digest "Dig 1" of the commercial range SPF did not contain trisodium pyrophosphate.

4.1.3. The coating formulas of Experimental Diets 18 and 19, and Control Diet A are described in Table 16 below wherein percentages are expressed by weight of the Experimental Diets.

TABLE 16

| Formulation of Diets | Exp. Diet 18 | Exp. Diet 19 | Control Diet A |
|---|---|---|---|
| Poultry fat | 6% | 6% | 6% |
| PEC 18 | 3% | | |
| PEC 19 | | 3% | |
| Liquid Poultry Digest « Dig 1 » | | | 3% |

4.1.4. Palatability results are presented below in Table 17.

TABLE 17

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| Without heating | | | | | | | | |
| Day 1 | Control Diet A | 0% | Experimental Diet 19 | 3.60% | 34 | 66 | *** | 34 |
| Day 2 | | | | | 35 | 65 | ** | 35 |
| With heating | | | | | | | | |
| Day 1 | Control Diet A | 0% | Experimental Diet 18 | 3.60% | 31 | 69 | *** | 36 |
| Day 2 | | | | | 31 | 69 | *** | 37 |
| With heating vs Without heating | | | | | | | | |
| Day 1 | Experimental Diet 18 | 3.60% | Experimental Diet 19 | 3.60% | 70 | 30 | *** | 36 |
| Day 2 | | | | | 57 | 43 | NS | 38 |

% A: average consumption of Food A;
% B: average consumption of Food B.

As shown in Table 17, food consumptions are significantly different between Control Diet and Experimental Diets, demonstrating the higher palatability to cats of Experimental Diets coated with liquid PECs including liquid PEs having a ratio AAS/AAT of less or equal to 12.80% and prepared by a method comprising or not a thermal treatment.

Nevertheless, these results also show that food consumption is significantly different between Experimental Diet 18 and Experimental Diet 19, demonstrating the higher palatability to cats of Experimental Diet 18 coated with a liquid PEC including a thermally-treated liquid PE.

Example 4.2: Assessment of the Palatability-Enhancing Effect of Liquid PECs Including Liquid PEs Characterized by Their Ratio AAS/AAT and Prepared by a Method Including Variations of the Thermal Treatment Conditions 4.2.1. In this Example, 3 liquid PEs were prepared by a method comprising variations of the thermal treatment conditions.

Liquid PEs 15 and 16 have the same formulation as liquid PE 13 described in Example 4.1 above, but the method for their preparation did not comprise the same thermal treatment. Thus, as liquid PE 13, liquid PEs 15 and 16 comprised an amino reactant having an AAS/AAT ratio of 3.60%

The ingredients of PE 15 or 16 were mixed and the pH was adjusted to a value of 7.5 by addition of NaOH solution. For PE 15, the mixture was heated at 150° C. during 1 minute. For PE 16, the mixture was heated at 180° C. during 1 minute. Then, the temperature was cooled down at less than 40° C., thereby obtaining liquid PE 15 or 16.

The formulation of liquid PE 13 (and thus of liquid PEs 15 and 16) is described in Table 14, Example 4.1.

4.2.2. The formulations of PECs 20, 21, and 22 are described in Table 18 below wherein percentages are expressed by weight of the PECs.

TABLE 18

| Formulation of PEC | PEC 20 | PEC 21 | PEC 22 |
|---|---|---|---|
| PE 13 | 5% | | |
| PE 15 | | 5% | |
| PE 16 | | | 5% |
| Liquid Poultry digest "Dig 1" (8) | 95% | 95% | 95% |

(8) The liquid poultry digest "Dig 1" of the commercial range SPF did not contain trisodium pyrophosphate.

4.2.3. The coating formulas of Experimental Diets 20, 21, and 22 and Control Diet B are described in Table 19 below wherein percentages are expressed by weight of the Experimental Diets.

TABLE 19

| Formulation of Diets | Exp. Diet 20 | Exp. Diet 21 | Exp. Diet 22 | Control Diet B |
|---|---|---|---|---|
| Poultry fat | 6% | 6% | 6% | 6% |
| PEC 20 | 3% | | | |
| PEC 21 | | 3% | | |
| PEC 22 | | | 3% | |
| Liquid Poultry digest « Dig 1 » | | | | 3% |
| Dry poultry digest « Dig 3 » (9) | 0.75% | 0.75% | 0.75% | 0.75% |

(9) The dry poultry digest "Dig 3" of the commercial range SPF contained trisodium pyrophosphate.

4.2.4. The palatability results are presented in Table 20 below.

TABLE 20

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| Day 1 | Control | 0% | Experimental | 3.60% | 26 | 74 | *** | 40 |
| Day 2 | Diet B | | Diet 20 | | 28 | 72 | *** | 40 |
| Day 1 | Control | 0% | Experimental | 3.60% | 32 | 68 | *** | 40 |
| Day 2 | Diet B | | Diet 21 | | 25 | 75 | *** | 40 |
| Day 1 | Control | 0% | Experimental | 3.60% | 38 | 62 | ** | 40 |
| Day 2 | Diet B | | Diet 22 | | 45 | 55 | NS | 40 |

As shown in Table 20, food consumptions are significantly different between Experimental Diets and Control Diet, demonstrating the higher palatability to cats of Experimental Diets coated with liquid PECs including liquid PEs having a ratio AAS/AAT of less or equal to 12.80% and prepared by a method comprising a thermal treatment performed under different conditions.

Example 5: Assessment of the Palatability-Enhancing Effect of Liquid PECs Having Different Animal Digest Contents and Including Liquid PEs Characterized by Their Ratio AAS/AAT 5.1. In this Example, the palatability-enhancing effect of a liquid PEC containing liquid animal digest of the SPF commercial range and different amounts of liquid PE 1 described in Example 1 above (characterized by an AAS/AAT ratio of 3.16%) was assessed.

Formulation and method of preparation of liquid PE 1 are described in Example 1 above.

5.2. The formulations of PECs 23, 24, and 25 are described in Table 21 below wherein percentages are expressed by weight of the PECs.

TABLE 21

| Formulation of PEC | PEC 23 | PEC 24 | PEC 25 |
|---|---|---|---|
| PE 1 | 5% | 45% | 90.1% |
| Liquid pork digest « Dig 2 » (10) | 85.10% | 45.1% | |
| Trisodium Pyrophosphate | 9.90% | 9.90% | 9.90% |

(10) The liquid pork digest "Dig 2" of the commercial range SPF contained trisodium pyrophosphate.

5.3. The coating formulas of Experimental Diets 23, 24, and 25 and Control Diet C are described in Table 22 below wherein percentages are expressed by weight of the Experimental Diets.

TABLE 22

| Formulation of Diets | Exp. Diet 23 | Exp. Diet 24 | Exp. Diet 25 | Control Diet C |
|---|---|---|---|---|
| Poultry fat | 6% | 6% | 6% | 6% |
| PEC 23 | 2% | | | |
| PEC 24 | | 2% | | |
| PEC 25 | | | 2% | |
| Liquid pork digest « Dig 2 » | | | | 2% |

5.4. The cat foods were presented to cats for palatability assessment. The palatability results are presented in Table 23 below.

TABLE 23

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| Day 1 | Control | 0% | Experimental | 3.16% | 39 | 61 | * | 38 |
| Day 2 | Diet C | | Diet 23 | | 38 | 62 | ** | 40 |
| Day 1 | Control | 0% | Experimental | 3.16% | 20 | 80 | *** | 39 |
| Day 2 | Diet C | | Diet 24 | | 17 | 83 | *** | 39 |
| Day 1 | Control | 0% | Experimental | 3.16% | 30 | 70 | *** | 40 |
| Day 2 | Diet C | | Diet 25 | | 24 | 76 | *** | 40 |

% A: average consumption of Food A;
% B: average consumption of Food B.

As shown in Table 23, food consumptions are significantly different between Experimental Diets and Control Diet, demonstrating the palatability-enhancing effect of liquid PECs having different animal digest contents and including liquid PEs characterized by a ratio AAS/AAT of less or equal to 12.80%.

Example 6: Assessment of the Palatability-Enhancing Effect of a Liquid PEC Applied at Different Levels and Including a PE Characterized by its Ratio AAS/AAT 6.1. In this Example, the palatability-enhancing effect of liquid PEC 26 applied at different levels in the experimental diets and including PE 17 characterized by an AAS/AAT ratio of 2.73% was assessed.

6.2. The formulation of PE 17 is described in Table 24 below:

TABLE 24

| Formulation of PE | PE 17 |
|---|---|
| Inactive dry yeast | 26.5 |
| Carbonyl compound 2* = material containing carbonyl groups | 34 |
| Water | 39.5 |

*Carbonyl compound 2: contained minimum 25% of mono- and/or disaccharides and/or oligosaccharides 6.3. Liquid PE 17 was prepared using the following method.

The ingredients of PE 17 formula were mixed and the pH was adjusted to a value of 7.5 by addition of 30% NaOH solution. The mixture was heated at 120° C. during 20 minutes. Afterwards the temperature was cooled down at less than 40° C.

6.4. The formulations of PEC 26 is described in Table 25 below wherein percentages are expressed by weight of the PECs.

TABLE 25

| Formulation of PEC | PEC 26 |
|---|---|
| Liquid pork digest S (11) | 74.7 |
| PE 17 | 12 |
| Trisodium pyrophosphate | 13.3 |

(11) The liquid pork digest S did not contain trisodium pyrophosphate.

6.5 The coating formulas of Experimental Diets 26 and 27 and Control Diet C are described in Table 26 below wherein percentages are expressed by weight of the Experimental Diets.

TABLE 26

| Formulation of Diets | Exp. Diet 26 | Exp. Diet 27 | Control Diet C |
|---|---|---|---|
| Poultry fat | 6% | 6% | 6% |
| PEC 26 | 1.4% | | |
| PEC 26 | | 2% | |
| Liquid pork digest « Dig 2 » (13) | | | 2% |

(13) The liquid pork digest "Dig 2" of the commercial range SPF contained trisodium pyrophosphate.

6.6. The palatability results are presented in Table 27 below.

TABLE 27

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| Day 1 | Control diet C | 0% | Experimental Diet 26 | 2.73% | 33 | 67 | *** | 39 |
| Day 2 | | | | | 40 | 60 | * | 39 |
| Day 1 | Control diet C | 0% | Experimental Diet 27 | 2.73% | 38 | 62 | *** | 36 |
| Day 2 | | | | | 33 | 67 | *** | 31 |

As shown in Table 27, food consumptions are significantly different between Experimental Diets and Control Diet, demonstrating the palatability-enhancing effect of liquid PEC 26 applied at different levels in the experimental diets and including PE 17 characterized by an AAS/AAT ratio of less or equal to 12.80%.

Example 7: Assessment of the Palatability-Enhancing Effect of a Dry PE Characterized by its Ratio AAS/AAT, This PE Being Applied by Inclusion in the Experimental Diet 7.1. In this Example, the palatability-enhancing effect of a dry PE, PE 18, characterized by its ratio AAS/AAT, and being applied by inclusion in the experimental diet, was assessed.

7.2. Preparation of PE 18

PE 18 was obtained after drying of the liquid PE 17, characterized by an AAS/AAT ratio of 2.73%, and described in Example 6 above (Table 24).

The liquid PE 17 was maintained at 80° C. and not cooled to ambient temperature in order to be directly dried by using a spray drier and a powder, PE 18, was then obtained (Humidity <6%). The ratio AAS/AAT was the same than in the liquid form since only water was evaporated from the composition.

7.3. Preparation of Diets

This PE 18 was then used in a Super Premium Cat Diet formulation by direct inclusion at 1% within the core raw materials, before the extrusion process and the Experimental Diet 28 was obtained. The control diet F in this example was exactly the same diet but without the inclusion of PE 18.

The coating formulas of Experimental Diets 28 and Control Diet F are described in Table 28 below wherein percentages are expressed by weight of the Diets.

TABLE 28

| Compositions of Diets | Exp. Diet 28 | Control Diet F |
|---|---|---|
| Amount of PE 18 inside the kibble | 1% | — |
| Coated poultry Fat | 6% | 6% |
| Liquid poultry digest « Dig 1 » (14) | 3% | 3% |
| Dry poultry digest « Dig 3 » (15) | 2% | 2% |

(14) The liquid poultry digest "Dig 1" of the commercial range SPF did not contain trisodium pyrophosphate.
(15) The dry poultry digest "Dig 3" of the commercial range SPF contained trisodium pyrophosphate.

7.4. Analytical composition of diets

Experimental diet 28 and control diet F were analyzed. As illustrated by Table 29 below, characteristics of both diets are very similar to each other, the amount of inclusion of PE 18 being very low (1%) and all components of the Diet formulation (meat flour, wheat, corn, etc.) being equally substituted.

TABLE 29

| Analytical data of Diets (%) | Exp. Diet 28 | Control Diet F |
|---|---|---|
| Moisture % | 7.7 | 7.8 |
| Proteins % | 35.6 | 36 |
| Fat % | 13.3 | 13.2 |
| Ashes % | 6.5 | 6.5 |
| Starch % | 7.8 | 7.7 |

7.5. The palatability results are presented in Table 30 below.

TABLE 30

| Test day | Food A | AAS/AAT ratio of corresponding PE | Food B | AAS/AAT ratio of corresponding PE | % A | % B | Statistical significance | Number of validated animals |
|---|---|---|---|---|---|---|---|---|
| Day 1 | Control diet F | 0% | Experimental Diet 28 | 2.73% | 42 | 58 | S | 40 |
| Day 2 | | | | | 50 | 50 | NS | 39 |

As shown in Table 30, food consumptions were significantly different the 1st day between Experimental Diet 28 and Control Diet, demonstrating the palatability-enhancing effect of dry PE 18 characterized by a ratio AAS/AAT of 2.73%.

The invention claimed is:

1. A method for preparing a palatability-enhancing composition comprising:
   a) mixing in an aqueous medium at least one amino reactant consisting of free amino acids (AAT) including sulfur-containing free amino acids (AAS), wherein a ratio of AAS/AAT of sulfur-containing free amino acids (AAS) to total free amino acids (AAT) is from 2.5% to 12.8% by weight based on the total weight of free amino acids, and at least one carbonyl composition comprising more than 20% and up to 100% by weight of monosaccharides and/or disaccharides and/or oligosaccharides to provide at least one non-fatty palatability enhancer, wherein the at least one non-fatty palatability enhancer does not contain any added or exogenous fat;
   thermally treating said at least one non-fatty palatability enhancer;
   b) mixing said at least one non-fatty palatability enhancer with one or more palatability-enhancing ingredients comprising at least one fat;
   c) optionally, drying the thus obtained mixture; and
   d) obtaining said palatability-enhancing composition;
   wherein said palatability-enhancing composition increases palatability to cats when added to cat food.

2. The method of claim 1, wherein the step c) is required.

3. The method of claim 1, further comprising, after said step a), a step a1) of drying said at least one non-fatty palatability enhancer.

4. A method for preparing a cat food with a palatability-enhancing composition, comprising:
   a) mixing in an aqueous medium at least one amino reactant consisting of free amino acids (AAT) including sulfur-containing free amino acids (AAS), wherein a ratio of AAS/AAT of sulfur-containing free amino acids (AAS) to total free amino acids (AAT) is from 2.5% to 12.8% by weight based on the total weight of free amino acids, and at least one carbonyl composition comprising more than 20% and up to 100% by weight of monosaccharides and/or disaccharides and/or oligosaccharides to provide at least one non-fatty palatability enhancer, wherein the at least one non-fatty palatability enhancer does not contain any added or exogenous fat;
   thermally treating said at least one non-fatty palatability enhancer;
   b) mixing said at least one non-fatty palatability enhancer with one or more palatability-enhancing ingredients comprising at least one fat;
   c) optionally, drying the thus obtained mixture;
   d) obtaining said palatability-enhancing composition; and
   e) adding said palatability-enhancing composition to cat food to increase palatability of the cat food to cats.

\* \* \* \* \*